(12) United States Patent
Boettger et al.

(10) Patent No.: US 9,014,338 B2
(45) Date of Patent: Apr. 21, 2015

(54) METHOD FOR DETERMINING A 4D PLAN FOR CARRYING OUT INTENSITY-MODULATED RADIATION THERAPY

(71) Applicants: Thomas Boettger, Heidelberg (DE); Johannes Fieres, Heidelberg (DE); Alexander Gemmel, Erlangen (DE); Iwan Kawrakow, Ljulin (BG)

(72) Inventors: Thomas Boettger, Heidelberg (DE); Johannes Fieres, Heidelberg (DE); Alexander Gemmel, Erlangen (DE); Iwan Kawrakow, Ljulin (BG)

(73) Assignee: Siemens Aktiengesellschaft, München (DE)

( * ) Notice: Subject to any disclaimer, the term of this patent is extended or adjusted under 35 U.S.C. 154(b) by 262 days.

(21) Appl. No.: 13/738,719

(22) Filed: Jan. 10, 2013

(65) Prior Publication Data

US 2013/0177135 A1     Jul. 11, 2013

(30) Foreign Application Priority Data

Jan. 11, 2012  (DE) .......................... 10 2012 200 297

(51) Int. Cl.
*G21K 5/04*   (2006.01)
*A61N 5/10*   (2006.01)

(52) U.S. Cl.
CPC .................................... *A61N 5/1037* (2013.01)

(58) Field of Classification Search
USPC ......... 378/145, 146, 147, 148, 149, 150, 151, 378/152, 153, 156, 157, 158, 159, 160, 161, 378/162; 382/128, 130, 131, 132, 276, 277, 382/278, 279, 285
See application file for complete search history.

(56) References Cited

U.S. PATENT DOCUMENTS

| 7,835,493 | B2 | 11/2010 | Keall et al. | |
|---|---|---|---|---|
| 7,894,574 | B1 | 2/2011 | Nord et al. | |
| 2008/0159478 | A1* | 7/2008 | Keall et al. | 378/65 |
| 2009/0041188 | A1* | 2/2009 | Keall et al. | 378/65 |
| 2009/0052623 | A1* | 2/2009 | Tome et al. | 378/65 |

OTHER PUBLICATIONS

German Office Action dated Dec. 14, 2012 for corresponding German Patent Application No. DE 10 2012 200 297.9, with English translation.

Gui, M., et al., "Four-Dimensional Intensity-Modulated Radiation Therapy Planning for Dynamic Tracking Using a Direct Aperture Deformation (DAD) Method," Med. Phys. vol. 37, No. 5, pp. 1966-1975 (2010).

(Continued)

*Primary Examiner* — Nicole Ippolito
(74) *Attorney, Agent, or Firm* — Lempia Summerfield Katz LLC

(57) ABSTRACT

A method for determining a 4D plan for carrying out intensity-modulated radiation therapy of a target volume subject to irregular periodic motion, with a radiation therapy apparatus is provided. The method includes selecting positions of a radiation source. The number of positions is selected to be identical in all 3D radiation therapy plans. The method also includes selecting a number of respective aperture settings assigned to a respective position of the radiation source to be identical in all 3D radiation therapy plans. A geometrical, temporal, and/or dynamic restriction that restricts a change of the aperture from one aperture setting to another aperture setting is predetermined, and the 3D radiation therapy plans are determined such that the 3D radiation therapy plans fulfill predetermined restrictions for aperture settings in each case.

20 Claims, 1 Drawing Sheet

---

A number m of positions $POS_j$ of the radiation source are predetermined identically for all 3D radiation therapy plans $BP_i$  — 101

A number w of respective aperture settings $AP_k$ are selected identically in all 3D radiation therapy plans $BP_i$ — 102

A geometrical and/or temporal and/or dynamic restriction is predetermined — 103

The 3D radiation therapy plans $BP_i$ are determined by using an optimization method — 104

(56) References Cited

OTHER PUBLICATIONS

Sheperd, D., et al., "Direct Aperture Optimization: A Turnkey Solution for Step-and-Shoot IMRT," Med. Phys. vol. 29, No. 6, pp. 1007-1018 (2002).

Jin, R., et al., "A Novel Fluence Map Optimization Model Incorporating Leaf Sequencing Constraints," Phys. Med. Biol., vol. 55, pp. 1243-1264 (2010).

Zhang, Y., et al., "Fluence Map Optimization in IMRT Cancer Treatment Planning and a Geometric Approach," National Cancer Institute, National Science Foundation (http://www.caam.rice.edu/~zhang/reports/tr0412.pdf) 2004.

Nohadani. 0., et al., "Motion Management with Phase Adapted 4D Optimization," Physics in Medicine and Biology, vol. 55, No. 17, pp. 5189-5202 (2010).

* cited by examiner

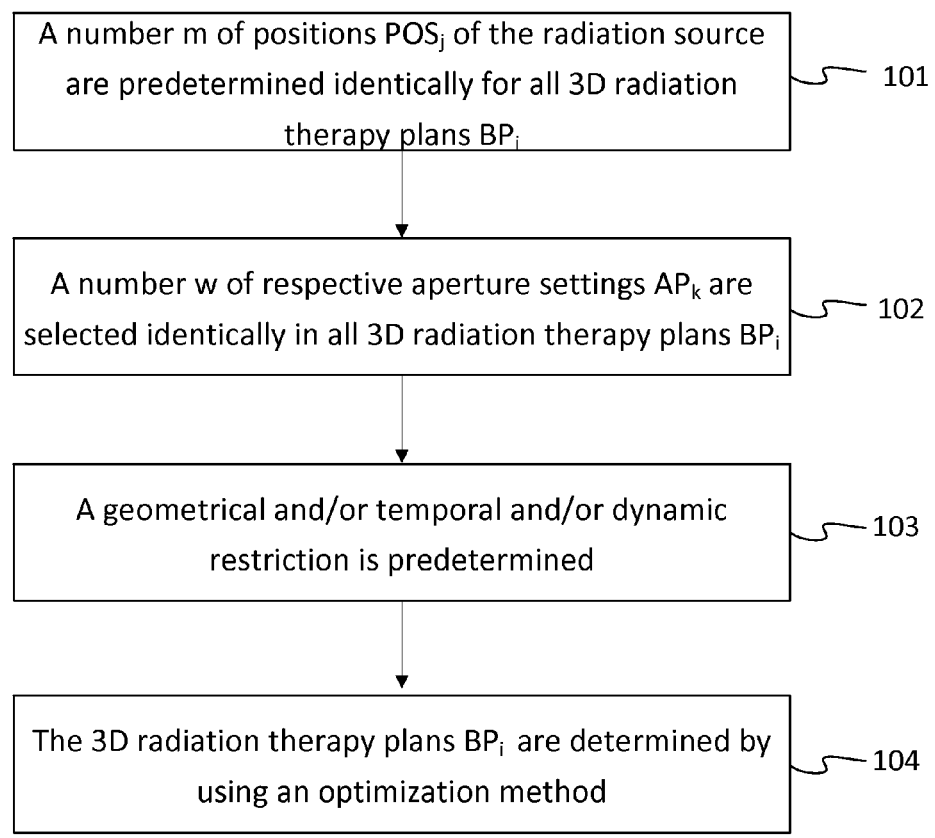

METHOD FOR DETERMINING A 4D PLAN FOR CARRYING OUT INTENSITY-MODULATED RADIATION THERAPY

This application claims the benefit of DE 10 2012 200 297.9, filed Jan. 11, 2012, which is hereby incorporated by reference.

BACKGROUND

The present embodiments relate to a method for determining a four-dimensional (4D) plan for carrying out intensity-modulated radiation therapy of a target volume with irregular periodic motion, with a radiation therapy apparatus.

Methods for determining 4D plans for Intensity-Modulated Radiation Therapy (IMRT; including static IMRT, dynamic IMRT, arc IMRT (IMAT) and hybrid IMRT) are known in the prior art.

In a 4D plan, the 3D radiation plans contained in the 4D plan are optimized in each case for the assigned motion phase. It is assumed in such cases that the target volume moves while the radiation therapy is being carried out in a manner, on which the planning is based.

In reality, however, discrepancies occur between the motion of the target volume underlying the planning and the motion of the target volume while radiation therapy is being carried out. Thus, for example, the motion of a lung tumor (e.g., a target volume) depends on the breathing motion of the lungs. If the breathing motion of a patient on whom the 4D plan is based differs from the breathing motion of the patient when the radiation therapy is being carried out, then radiation therapy carried out in accordance with the 4D plan does not lead to the desired radiation therapy results. The 4D plans may therefore be robust in relation to motion discrepancies of the target volume from the motion underlying the 4D plan.

The collimators used for beam forming (e.g., multi-leaf collimators (MLC)) are subject to restrictions during a change from one aperture setting to a next aperture setting. Thus, for example, the leaves of a multi-leaf collimator are moveable at a given maximum speed, so that a change from an aperture setting to a next aperture setting uses a minimum time. The 4D plans may, therefore, also be determined to take account of the restrictions of the collimator.

In order to solve these problems, the article "Motion management with phase-adapted 4D-optimization," by Omid Nohadani et al., in Phys. Med. Biol. 55 (2010) 5189-5202 proposes a method for determining 4D radiation therapy plans that is designed to be robust in relation to irregular motion discrepancies. The method is based on determining fluence maps optimized towards the therapy objective. The method is restricted by fluence maps for adjacent motion phases. On the basis of the fluence map aperture settings of a collimator with adjustable aperture (e.g., MLC) are then determined for the 4D plan. It is assumed that similar fluence maps, when converted into aperture settings, create similar apertures. The 4D plan thus defines a plurality of positions of the radiation source aperture settings of the collimator assigned to these positions, which are produced on the basis of optimized fluence maps.

On the subject of "optimization of fluence maps," "Fluence Map Optimization in IMRT Cancer Treatment Planning and A Geometric Approach," by Yin Zhang and Michael Merrit, July 2004, revised May 2005, National Cancer Institute, National Science Foundation, (http://www.caam.rice.edu/~zhang/reports/tr0412.pdf) is provided.

SUMMARY AND DESCRIPTION

The present embodiments may obviate one or more of the drawbacks or limitations in the related art. For example, an alternate method for determining a four-dimensional (4D) plan for carrying out intensity-modulated radiation therapy that may be performed with less effort and with which a robust 4D plan with respect to irregular movements is determinable, is provided.

By contrast with the cited prior art, the present embodiments are based on optimizing the 4D plan directly with respect to predetermined restrictions during changes to the aperture of the collimator.

One embodiment of a method for determining a 4D plan for carrying out intensity-modulated radiation therapy of a target volume with periodic irregular motion, with a radiation therapy apparatus is provided. The radiation therapy apparatus includes a radiation source that is moveable around the target volume and a collimator with an adjustable aperture for beam forming of a radiation beam emanating from the radiation source. The irregular periodic motion of the target volume has a number of phases $PH_i$ with a given phase sequence. The 4D plan includes a respective 3D radiation therapy plan $BP_i$ for each phase $PH_i$ that defines a plurality of positions $POS_j$ of the radiation source and the aperture settings AP of the collimator assigned to the positions $POS_j$. Positions $POS_j$ of the radiation source and the number of positions m are selected to be identical in all 3D radiation therapy plans $BP_i$:

$$POS_j = POS_{i,j};$$

$$POS_{i=1,j} = POS_{i=2,j} = POS_{i=3,j} = \ldots = POS_{n,j};$$

with:

Radiation therapy plan index i=1, 2, ..., n; and

Position index j=1, 2, ..., m, and

A number w of aperture settings $AP_k$ assigned to a position $POS_{i,j}$ of the radiation source is selected to be identical in all 3D radiation therapy plans $BP_i$:

$$AP_k = AP_{i,j,k}$$

with:

Aperture setting index k=1, 2, ..., w.

Thus, the 4D plan includes a number n of 3D radiation therapy plans $BP_i$. Each of the n 3D radiation therapy plans $BP_i$ defines, for a number of m positions $POS_{i,j}$ of the radiation source, a respective number w of associated/assigned aperture settings $AP_{i,j,k}$. The positions $POS_j$ of the radiation source and the number of positions m are the same for all 3D radiation therapy plans. For each of the m positions $POS_j$, an n×w matrix of aperture settings $AP_{i,j,k}$ may thus be set up:

$POS_j$:

| | k = 1 | k = 2 | k = 3 | ... | k = w |
|---|---|---|---|---|---|
| i = 1 | $AP_{1,j,1}$ | $AP_{1,j,2}$ | $AP_{1,j,3}$ | ... | $AP_{1,j,w}$ |
| i = 2 | $AP_{2,j,1}$ | $AP_{2,j,2}$ | $AP_{2,j,3}$ | ... | $AP_{2,j,w}$ |
| ... | ... | ... | ... | ... | ... |
| i = n | $AP_{n,j,1}$ | $AP_{n,j,2}$ | $AP_{n,j,3}$ | ... | $AP_{n,j,w}$ |

In one embodiment, a geometrical, and/or temporal, and/or dynamic restriction is also predetermined. The restriction restricts a change of the aperture from one aperture setting to another aperture setting. The predetermined restriction depends in such cases on the collimator currently being used and may depend on how the collimator is controlled. A suitable choice of restriction enables the 4D plan to be optimized with respect to the shortest possible execution time or the greatest possible robustness in relation to the motion discrepancies described at the outset.

The 3D radiation therapy plans $BP_i$ are determined such that the following applies for aperture settings $AP_{i,j,k}$ of the 3D radiation therapy plans:

$AP_{i,j,k}$ and $AP_{i+1,j,k}$ fulfill the predetermined restriction for all $i=1, 2, \ldots, n-1$; and/or $AP_{i,j,k}$ and $AP_{i,j,k+1}$ fulfill the predetermined restriction for all $k=1, 2, \ldots, w-1$; and/or $AP_{i,j,k}$ and $AP_{i+1,j,k+1}$ fulfill the predetermined restriction for all $i=1, 2, \ldots, n-1$ and $k=1, 2, \ldots, w-1$.

Transferred to the n×w matrix of the aperture settings $AP_{i,j,k}$ given above, this provides that in the n×w matrix, aperture settings disposed next to one another in a column (a)) and/or a row (b)) and/or diagonal (c)) fulfils a predetermined restriction and are thus similar to one another. Aperture settings that may fulfill the restriction may, for example, quickly be changed into one another, so that the execution time of the 4D plan is minimizable.

In one embodiment of the method, the 3D radiation therapy plans $BP_i$ are determined such that the following additionally applies:

$AP_{i,j,k}$ and $AP_{i+2,j,k}$ fulfill the restriction for all $i=1, 2, \ldots, n-2$; and/or $AP_{i,j,k}$ and $AP_{i,j,k+2}$ fulfill the restriction for all $k=1, 2, \ldots, w-2$; and/or $AP_{i,j,k}$ and $AP_{i+2,j,k+2}$ fulfill the restriction for all $i=1, 2, \ldots, n-2$ and $k=1, 2, \ldots, w-2$.

Transferred to the n×w matrix of the aperture settings $AP_{i,j,k}$ given above, the aperture settings of the first and second order disposed next to one another in the n×w-matrix in a column (d)) and/or a row (e)) and/or diagonal (f)) fulfill the predetermined restriction and are therefore similar to one another.

A further development is characterized in that the 3D radiation plans are determined such that the following applies:
$AP_{i,j,k=w}$ and $AP_{i+1,j,k=1}$ fulfill the restriction; and
$AP_{i=n,j,k=w}$ and $AP_{i=1,j,k=1}$ fulfill the restriction.

The aperture settings $AP_{i,j,k}$ may be determined such that, for the 4D plan (e.g., all the 3D radiation therapy plans $BP_i$), an iterative optimization method is carried out. Corresponding positions of the radiation source in the individual 3D radiation therapy plans are each initialized with identical aperture settings $AP_0$, and on this basis, the aperture settings $AP_{i,j,k}$ are optimized with respect to predetermined therapy goals of the 4D plan and under the existing conditions. Corresponding optimization algorithms are known in the prior art.

In one embodiment, the collimator is a multi-leaf collimator (MLC) with adjustable leaves. In this case, a leaf setting of all the leaves of the multi-leaf collimator corresponds to an aperture setting. The predetermined restriction may specify a leaf speed in this case (e.g., a maximum leaf speed). In such cases, it is assumed that all leaves of the multi-leaf collimator may be moved at the same maximum speed. If this is not the case, individual restrictions per leaf may also be predetermined. The restriction may, for example, define a maximum leaf position. If the difference in leaf position for one aperture setting to a next aperture setting is too large, the restriction is not fulfilled, and the aperture settings are to be further optimized until the predetermined conditions/restrictions are fulfilled.

In one embodiment of the method, the 3D radiation therapy plans $BP_i$ are determined such that a radiation dose generated by an execution of one of the respective 3D radiation therapy plans is identical for all 3D radiation therapy plans $BP_i$. In addition, an embodiment of the method includes determining the 3D radiation therapy plans $BP_i$ such that a radiation dose distribution in the target volume created by execution of one of the respective 3D radiation therapy plans $BP_i$ is identical for all 3D radiation therapy plans $BP_i$.

Since the radiation dose and/or the radiation dose distribution of the fully irradiated 4D plan in the target volume may always also be expressed as an overlaying of a radiation dose/radiation dose distribution onto the radiation dose/radiation dose distribution arising during the irradiation of the individual 3D radiation therapy plans, 3D radiation therapy plans determined in this way make additional flexibility in the implementation/execution of the 4D plan possible and also make the 4D plan more robust in relation to motion discrepancies (e.g., discrepancies in the phases, on which the planning is based, and the phases that actually occur during execution of the 4D plan).

A further development of the method includes determining the phases $PH_i$ on the basis of the irregular periodic motion of the target volume such that all phases $PH_i, i=1, 2, \ldots, n$ have an identical probability of occurring and/or have an identical temporal length. This increases the robustness of the 4D plan further since errors in the implementation of a 3D radiation therapy plan (e.g., in a phase PH) may not dominate the 4D plan or may only dominate the 4D plan to a limited extent.

The proposed method, by contrast with the prior art mentioned above, does not optimize the fluence distributions, but instead optimizes the collimator parameters directly.

BRIEF DESCRIPTION OF THE DRAWINGS

FIG. 1 shows a flow diagram of one embodiment of a method for determining a four-dimensional plan for carrying out intensity-modulated radiation therapy of a target volume.

DETAILED DESCRIPTION OF THE DRAWINGS

FIG. 1 shows a schematic flow diagram of one embodiment of a method for determining a four-dimensional (4D) plan for carrying out intensity-modulated radiation therapy of a target volume having an irregular periodic motion, with a radiation therapy apparatus. The radiation therapy apparatus includes a radiation source that is moveable around the target volume and a collimator with an adjustable aperture for beam forming of a beam of radiation emanating from the radiation source. The irregular periodic motion of the target volume has a number of phases $PH_i$ with a given phase sequence. For each phase $PH_i$, the 4D plan includes a respective 3D radiation therapy plan $BP_i$ that defines a plurality of positions $POS_j$ of the beam source and aperture settings AP of the collimator assigned to the positions.

In act 101, a number in of positions $POS_j$ of the radiation source are predetermined identically for all 3D radiation therapy plans $BP_i$, so that the following applies:

$POS_j = POS_{i,j}$ and $POS_{i=1,j} = POS_{i=2,j} = POS_{i=3,j} = \ldots = POS_{i=n,j}$, with radiation therapy plan index $i=1, 2, \ldots, n$, and position index $j=1, 2, \ldots, m$.

In act 102, a number w of respective aperture settings $AP_k$ assigned to a position $POS_{i,j}$ of the radiation source are selected identically in all 3D radiation therapy plans $BP_i$, so that the following applies: $AP_k=AP_{i,j,k}$, with aperture setting index k=1, 2, ..., w.

In act 103, a geometrical, and/or temporal, and/or dynamic restriction that restricts a change of the aperture from one aperture setting to another aperture setting is predetermined.

In act 104, the 3D radiation therapy plans $BP_i$ are determined by using an optimization method. In such cases, the aperture settings $AP_{i,j,k}$ are initialized for corresponding positions of the radiation source in the individual 3D radiation therapy plans with an identical aperture setting $AP_0$ in each case. On this basis, the aperture settings $AP_{i,j,k}$ are optimized with respect to predetermined therapy goals of the 4D plan and under the following conditions for aperture settings $AP_{i,j,k}$: $AP_{i,j,k}$ and $AP_{i+1,j,k}$ fulfill the restriction for all i=1, 2, ..., n−1; and $AP_{i,j,k}$ and $AP_{i,j,k+1}$ fulfill the restriction for all k=1, 2, ..., w−1; and $AP_{i,j,k}$ and $AP_{i+1,j,k+1}$ fulfill the restriction for all i=1, 2, ..., n−1 and k=1, 2, ..., w−1.

Although the invention has been illustrated and described in greater detail by the exemplary embodiments, the invention is not restricted by the disclosed examples, and other variations may be derived herefrom by the person skilled in the art without departing from the scope of protection of the invention.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a four-dimensional (4D) plan for carrying out intensity-modulated radiation therapy of a target volume having irregular periodic motion with a radiation therapy apparatus, the radiation therapy apparatus comprising a radiation source moveable around the target volume and a collimator with an adjustable aperture for beam forming of a beam of radiation emanating from the radiation source, wherein the irregular periodic motion of the target volume has a plurality of phases with a given phase sequence, for each phase of the plurality of phases, the 4D plan comprises a respective 3D radiation therapy plan that defines a plurality of positions of the radiation source and aperture settings of the collimator assigned to the plurality of positions, the method comprising:

selecting the plurality of positions of the radiation source, a number of positions of the radiation source being selected to be identical in all 3D radiation therapy plans; and selecting a number of the aperture settings assigned to a respective position of the plurality of positions of the radiation source to be identical in all 3D radiation therapy plans, wherein a restriction is predetermined, the restriction comprising a geometrical restriction, a temporal restriction, a dynamic restriction, or a combination thereof, the restriction restricting a change of the aperture from one aperture setting to another aperture setting.

2. The method as claimed in claim 1, wherein the 3D radiation therapy plans are determined such that, for the aperture settings, $AP_{i,j,k}$ and $AP_{i+1,j,k}$ fulfill the restriction for all i=1, 2, ..., n−1, $AP_{i,j,k}$ and $AP_{i,j,k+1}$ fulfill the restriction for all k=1, 2, ... w−1, and $AP_{i+1,j,k+1}$ fulfill the restriction for all i=1, 2, ..., n−1 and k=1, 2, ... w−1, or a combination thereof, and wherein AP represents the aperture settings, i is a radiation therapy plan index and is equal to 1, 2, ..., n, j is a position index and is equal to 1, 2, ..., m, and k is an aperture setting index and is equal to 1, 2, ... w.

3. The method as claimed in claim 2, wherein the 3D radiation therapy plans are determined such that $AP_{i,j,k}$ and $AP_{i+2,j,k}$ fulfill the restriction for all i=1, 2, ..., n−2, $AP_{i,j,k}$ and $AP_{i,j,k+2}$ fulfill the restriction for all k=1, 2, ..., w−2, $AP_{i,j,k}$ and $AP_{i+2,j,k+2}$ fulfill the restriction for all i=1, 2, ..., n−2 and k=1, 2, ..., w−2, or a combination thereof.

4. The method as claimed in claim 3, wherein the 3D radiation therapy plans are determined such that $AP_{i,j,k=w}$ and $AP_{i+1,j,k=1}$ fulfill the restriction, and $AP_{i=n,j,k=w}$ and $AP_{i=1,j,k=1}$ fulfill the restriction.

5. The method as claimed in claim 3, wherein the collimator is a multi-leaf collimator with adjustable leaves, and the restriction specifies at least a maximum leaf speed.

6. The method as claimed in claim 3, wherein the 3D radiation therapy plans are determined such that a radiation dose generated in each case by execution of one of the respective 3D radiation therapy plans in the target volume is identical for all 3D radiation therapy plans.

7. The method as claimed in claim 3, wherein the 3D radiation therapy plans are determined such that a radiation dose distribution generated in each case by execution of one of the respective 3D radiation therapy plans in the target volume is identical for all 3D radiation therapy plans.

8. The method as claimed in claim 3, wherein the plurality of phases are determined on the basis of the irregular periodic motion of the target volume such that all phases of the plurality of phases have an identical probability of occurring.

9. The method as claimed in claim 2, wherein the 3D radiation therapy plans are determined such that $AP_{i,j,k=w}$ and $AP_{i+1,j,k=1}$ fulfill the restriction, and $AP_{i=j,k=w}$ and $AP_{i=1,j,k=1}$ fulfill the restriction.

10. The method as claimed in claim 9, wherein the collimator is a multi-leaf collimator with adjustable leaves, and the restriction specifies at least a maximum leaf speed.

11. The method as claimed in claim 9, wherein the 3D radiation therapy plans are determined such that a radiation dose generated in each case by execution of one of the respective 3D radiation therapy plans in the target volume is identical for all 3D radiation therapy plans.

12. The method as claimed in claim 2, wherein the collimator is a multi-leaf collimator with adjustable leaves, and the restriction specifies at least a maximum leaf speed.

13. The method as claimed in claim 1, wherein the collimator is a multi-leaf collimator with adjustable leaves, and the restriction specifies at least a maximum leaf speed.

14. The method as claimed in claim 13, wherein the 3D radiation therapy plans are determined such that a radiation dose generated in each case by execution of one of the respective 3D radiation therapy plans in the target volume is identical for all 3D radiation therapy plans.

15. The method as claimed in claim 13, wherein the 3D radiation therapy plans are determined such that a radiation dose distribution generated in each case by execution of one of the respective 3D radiation therapy plans in the target volume is identical for all 3D radiation therapy plans.

16. The method as claimed in claim 1, wherein the 3D radiation therapy plans are determined such that a radiation dose generated in each case by execution of one of the respective 3D radiation therapy plans in the target volume is identical for all 3D radiation therapy plans.

17. The method as claimed in claim 16, wherein the 3D radiation therapy plans are determined such that a radiation dose distribution generated in each case by execution of one of the respective 3D radiation therapy plans in the target volume is identical for all 3D radiation therapy plans.

18. The method as claimed in claim 1, wherein the 3D radiation therapy plans are determined such that a radiation dose distribution generated in each case by execution of one of the respective 3D radiation therapy plans in the target volume is identical for all 3D radiation therapy plans.

19. The method as claimed in claim 1, wherein the plurality of phases are determined on the basis of the irregular periodic motion of the target volume such that all phases of the plurality of phases have an identical probability of occurring.

20. A method for determining a four-dimensional (4D) plan for carrying out intensity-modulated radiation therapy of a target volume having irregular periodic motion with a radiation therapy apparatus, the radiation therapy apparatus comprising a radiation source moveable around the target volume and a collimator with an adjustable aperture for beam forming of a beam of radiation emanating from the radiation source, wherein the irregular periodic motion of the target volume has a plurality of phases with a given phase sequence, for each phase of the plurality of phases, the 4D plan comprises a respective 3D radiation therapy plan that defines a plurality of positions of the radiation source and aperture settings of the collimator assigned to the plurality of positions, the method comprising:

selecting the plurality of positions of the radiation source, a number of positions of the radiation source being selected to be identical in all 3D radiation therapy plans; and selecting a number of the aperture settings assigned to a respective position of the plurality of positions of the radiation source to be identical in all 3D radiation therapy plans, wherein a restriction is predetermined, the restriction comprising a geometrical restriction, a temporal restriction, a dynamic restriction, or a combination thereof, the restriction restricting a change of the aperture from one aperture setting to another aperture setting, wherein the 3D radiation therapy plans are determined such that, for the aperture settings, $AP_{i,j,k}$ and $AP_{i+1,j,k}$ fulfill the restriction for all i=1, 2, ..., n−1, $AP_{i,j,k}$ and $AP_{i,j,k+1}$ fulfill the restriction for all k=1, 2, ..., w−1, $AP_{i,j,k}$ and $AP_{i+1,j,k+1}$ fulfill the restriction for all i=1, 2, ..., n−1 and k=1, 2, ..., w−1, or a combination thereof, and wherein AP represents the aperture settings, i is a radiation therapy plan index and is equal to 1, 2, ..., n, j is a position index and is equal to 1, 2, ..., m, and k is an aperture setting index and is equal to 1, 2, ... w.

* * * * *

UNITED STATES PATENT AND TRADEMARK OFFICE
CERTIFICATE OF CORRECTION

PATENT NO. : 9,014,338 B2  
APPLICATION NO. : 13/738719  
DATED : April 21, 2015  
INVENTOR(S) : Thomas Boettger et al.

Page 1 of 1

It is certified that error appears in the above-identified patent and that said Letters Patent is hereby corrected as shown below:

In the Claims:  
Claim 2, Column 6, line 1, insert --$AP_{i,j,k}$-- after "w-1,".

Signed and Sealed this  
Third Day of November, 2015

Michelle K. Lee  
*Director of the United States Patent and Trademark Office*